United States Patent [19]

Kaplan

[11] Patent Number: 4,687,484
[45] Date of Patent: Aug. 18, 1987

[54] ANTERIOR CHAMBER INTRAOCULAR LENS

[76] Inventor: Linda J. Kaplan, 2500 E. Hallandale Beach Blvd., Suite 207, Hallandale, Fla. 33009

[21] Appl. No.: 881,210

[22] Filed: Jul. 1, 1986

Related U.S. Application Data

[63] Continuation-in-part of Ser. No. 560,132, Dec. 12, 1983, abandoned.

[51] Int. Cl.⁴ .............................................. A61F 2/16
[52] U.S. Cl. ....................................................... 623/6
[58] Field of Search ............................................ 623/6

[56] References Cited

U.S. PATENT DOCUMENTS

| | | | |
|---|---|---|---|
| 4,242,760 | 1/1981 | Rainin | 623/6 |
| 4,298,994 | 11/1981 | Clayman | 623/6 |
| 4,338,687 | 7/1982 | Rainin | 623/6 |
| 4,437,194 | 3/1984 | Hahs | 623/6 |
| 4,527,294 | 7/1985 | Heslin | 623/6 |
| 4,536,895 | 8/1985 | Bittner | 623/6 |
| 4,543,673 | 10/1985 | Drake et al. | 623/6 |

FOREIGN PATENT DOCUMENTS

WO83/01568 5/1983 PCT Int'l Appl. ..................... 623/6

OTHER PUBLICATIONS

"Nuevos Modelos de Lentes Plasticas de Camara Anterior" by Barraquer, Joaquin, *Anales del Instituto Barraquer*, Sep. 1961, pp. 345-352.
"The Intraocular Implant Lens Development and Results with Special Reference to the Binkhurst Lens" by M. E. Nordlohne (Book) 2nd Edition, The Williams & Wilkins Co., Baltimore, 1975, pp. 14-20.

*Primary Examiner*—Ronald L. Frinks
*Attorney, Agent, or Firm*—Berman, Aisenberg & Platt

[57] ABSTRACT

In an intraocular lens for permanent implantation into the anterior chamber of any size of aphakic human eye, a lens optic portion is centrally placed and maintained in position in the anterior chamber of the eye by a plurality of flexible haptics connected to the lens optic portion, either directly or connected through a cylinder-spring arrangement, which allows the lens to be inserted in the eye through a very small incision, no greater than the smallest diameter of the lens optic portion. A rounded rectangular shape of lens optic is also described. The lens may alternatively be implanted into the posterior chamber of the eye.

15 Claims, 19 Drawing Figures

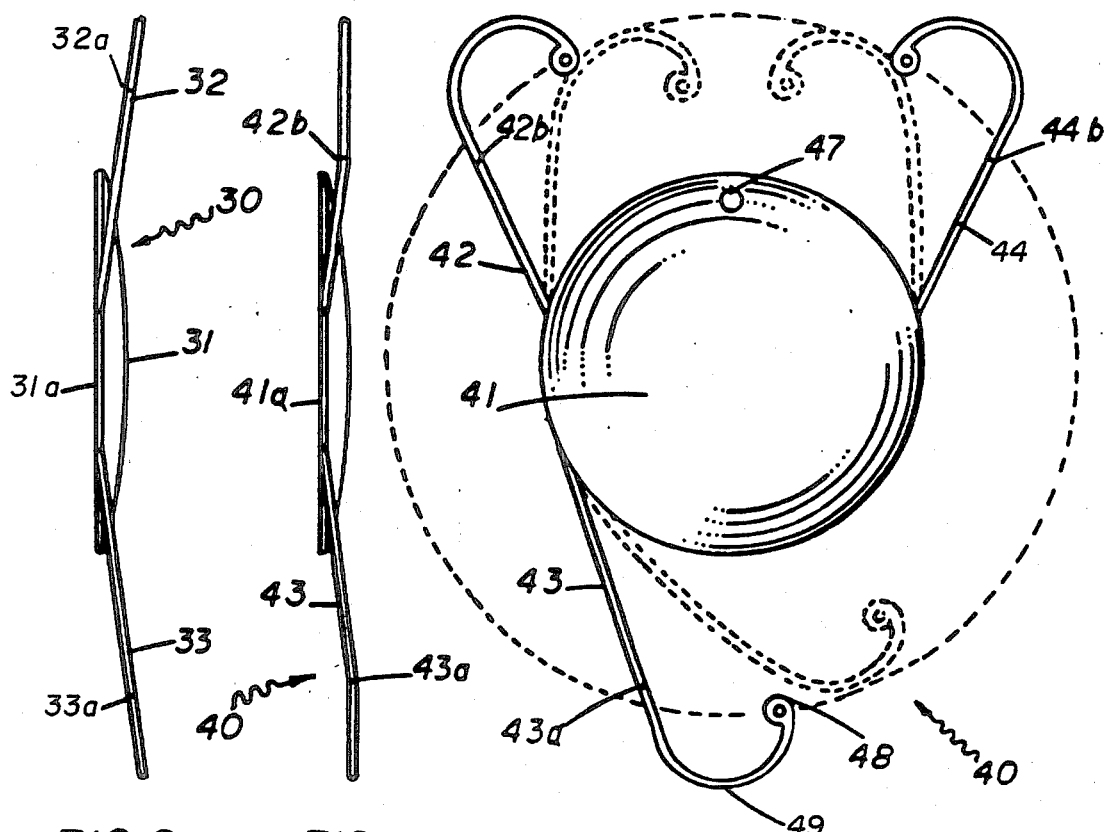

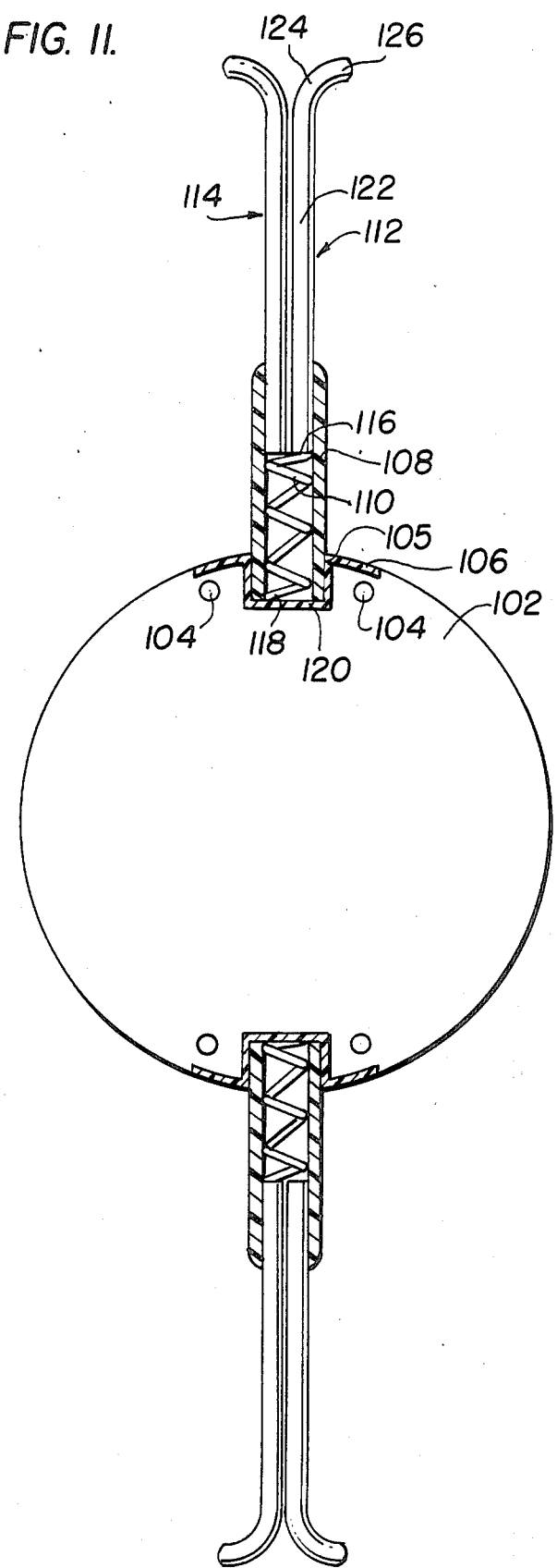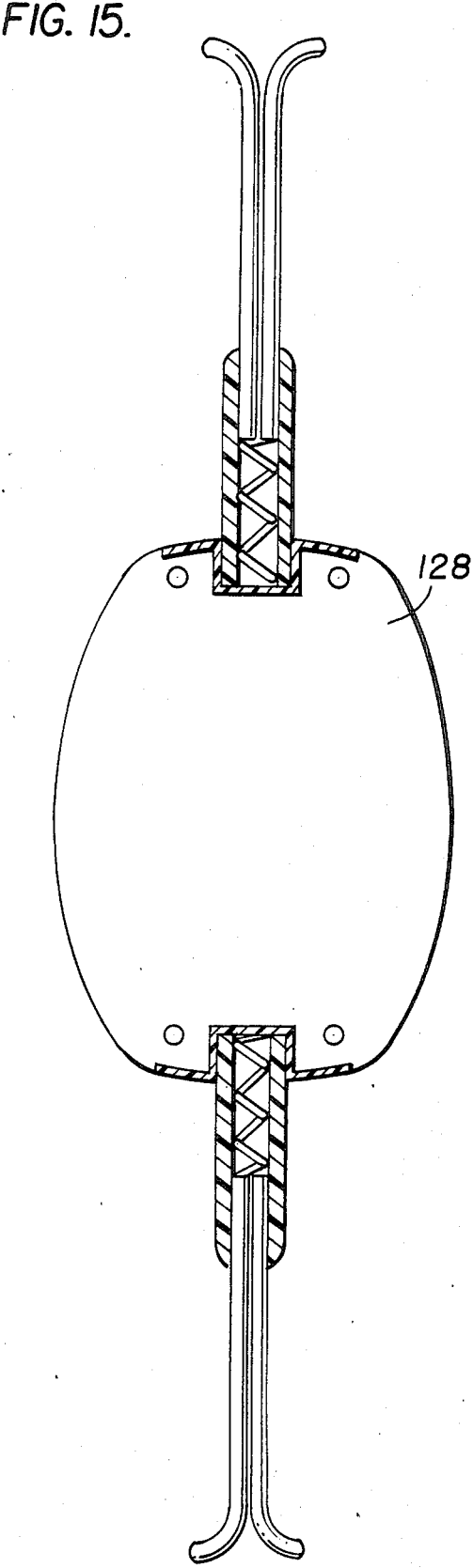

ANTERIOR CHAMBER INTRAOCULAR LENS

CROSS-REFERENCE TO RELATED APPLICATIONS

This application is a continuation-in-part of Ser. No. 560,132, filed Dec. 12, 1983, now abandoned.

FIELD OF THE INVENTION

This application relates to an intraocular lens for permanent implantation into the anterior chamber of an aphakic human eye.

BACKGROUND OF THE INVENTION

This invention relates to an intraocular lens for implantation into the anterior chamber of a human eye.

A large number of intraocular lenses have been described for implantation in the eye after cataract surgery, but none of them have been adequately successful in use. There are three common techniques for cataract surgery: intracapsular, where the entire lens is removed including the capsule; extracapsular, where the nucleus and cortex of the lens are removed, leaving the posterior portion of the capsule in place; and phakoemulsification, which often leaves the posterior capsule in place, and which is done through a very small incision. Lens implantation requires different surgical techniques for the different forms of cataract surgery. Microsurgical techniques are employed.

Problems have frequently arisen with prior art lenses. One problem is the requirement of a larger incision than is desirable, since this causes attendant pain and possible tissue damage. If an incision is too large, the anterior chamber of the eye may collapse and cause damage to the cornea. Also, since human eyes vary in size and shape, prior art lenses must be made in a variety of sizes and shapes to accommodate these differences. Errors in selecting the proper size of lens for each eye are quite common. Additionally, the cost of maintaining a large inventory of different sizes of lens is quite expensive.

Among the prior art lenses are those which claim the ability to be used in both the anterior and posterior chambers of the eye; this prevents optimal design for either chamber. Implantation needs vary between the two chambers and one lens cannot satisfactorily bridge these variances, due to differences in tissue structure and fixation properties.

An anterior chamber lens may be used after any type of cataract removal surgery, and is the only type of lens that can be used in many complicated cases.

The newer anterior chamber lenses are modeled after a lens introduced by Strampelli in 1953. These lenses cause complications due to difficult insertion, sizing and fixation, resulting in cornea damage, dislocation, hemorrhage and glaucoma. Rainin (U.S. Pat. No. 4,242,760), presented a new lens in 1979, which could be placed in either the anterior or posterior chamber of the eye. The haptics were always secured in the ciliary sulcus of the posterior chamber, since placement of the haptics of this lens into the anterior chamber would have projected the optic against the cornea. By definition, an anterior chamber lens is fixated in the anterior chamber by means of stabilization in front of the iris muscle tissue, and a posterior chamber lens is fixated in the posterior chamber by placement of the haptics behind the iris muscle tissue. The fixation of Rainin's lens (which is in the posterior chamber even if the lens itself is placed in the anterior chamber), is largely dependent upon support from the pupil and iris, and this can result in extensive inflammation, uveitis and glaucoma. The Rainin lens is not a true anterior chamber fixed lens.

Shepard and Copeland devised anterior chamber lenses with some degree of flexibility. Their usage has been limited by unnecessary tissue damage occuring since these lenses are both designed to be inserted through a large limbal incision which cuts through a large portion of the trabecular meshwork. The haptics, which are adjustable approximately 2 mm in length, traverse the remaining trabecular meshwork in the anterior chamber angle thereby damaging by traction that part of the trabecular meshwork which is not damaged by incision. The haptics collapse against the iris tissue, causing tearing and contributing to astigmatism postoperatively. Also, the haptics may pull, tear and break preplaced sutures at the incision, requiring additional surgical maneuvers.

Cilco has designed a variety of lenses for the anterior and posterior chamber. None of these lenses are suitable for insertion through a small incision, in which the incision need be no larger than the size of the optic.

The semi-flexible lens of Hahs, U.S. Pat. No. 4,437,194, is designed for implantation into the anterior or posterior chamber. This closed loop, double reinforced haptic design is very rigid and has limited compressibility for the anterior chamber, causing undue tissue tenderness due to the rigid design.

The intraocular lens of Drake, U.S. Pat. No. 4,543,673, also has a rigid design, using either three or four haptics.

SUMMARY OF THE INVENTION

An intraocular lens structure has been designed for permanent implantation into the anterior chamber of any size aphakic human eye. The lens optic is centrally placed and maintained in position in the anterior chamber by completely flexible haptics. The lens is inserted through a very small incision, no larger than the diameter of the lens and the flexible haptic arrangement allows for perfect fit of the lens into any size of eye, with maximal lens stability. The lens may also be implanted into the posterior chamber of an aphakic eye.

In one embodiment of this invention, a pair of closely spaced parallel haptics extends outwardly from one end of the optic and a similar pair extends in diametrically opposed position from the other end of the optic. In each pair one haptic has its open curved end portion curving outwardly in one direction and the other haptic has its end portion curving oppositely.

In a another embodiment of this invention, two similar haptics extend at spaced apart positions from the median portion of the optic so that their end portions curve toward one another, with the positioning hole of the optic being in between. A third similar haptic extends from a position near the point of attachment of one of the other two haptics but in the opposite direction, its open curved end portion being curved in the same direction as the remaining haptic. In both this and the preceding embodiment all the haptics are flexible and have their curved end portions offset from their connecting portions. This offset or "crimp" in design allows bending of the haptic at that site, and thus gives added flexibility for proper fit, ease of insertion and lens stability. Also, this flexibility in the lens design minimizes eye tenderness.

In a preferred embodiment, a cylinder-spring design eliminates tissue tenderness and ocular trauma during and after lens implantation. Pairs of haptics are secured to a compressible spring which is inserted within a cylinder into a housing in the lens optic. The spring and haptics extend outwardly from the lens through a cylinder, the effective length of the structure being reduced as the spring is compressed within the cylinder.

It is an object of this invention to provide a new, flexible intraocular lens having two opposing pairs of flexible haptics.

It is another object of the invention to provide a flexible, intraocular lens having a cylinder-spring mechanism to enable the lens to be implanted in an eye of any size.

It is a further object of this invention to provide an intraocular lens which is suitable for insertion in the anterior chamber of an eye after any type of cataract surgery.

It is still another object of the invention to provide an intraocular lens requiring an incision no larger than the diameter of the lens.

It is a still further object of the invention to provide an intraocular lens which may be of rounded rectangular shape.

BRIEF DESCRIPTION OF THE DRAWINGS

FIG. 6 is an end view of embodiment of the invention having three spaced haptics.

FIG. 7 is an end view of another embodiment having three spaced haptics, differently vaulted.

FIG. 8 is a side view of FIG. 6.

FIG. 9 is a side view of FIG. 7.

FIG. 10 is a top view of FIG. 7 in which the dotted lines illustrate how the haptics are compressed when inserted into the eye.

FIG. 11 is a top view of a circular optic, having two pairs of opposing haptics in the maximally non-compressed position.

FIG. 15 is a top view of a rectangular optic having two pairs of opposing haptics.

DETAILED DESCRIPTION OF THE INVENTION

The anterior chamber intraocular lens of the invention is inserted through an opening at the limbus, which is the junction of the cornea (clear window) and sclera (white eye wall). A small incision is advantageous, since if a large incision is used, the cornea is more likely to collapse due to the escape of fluid from the anterior chamber. The inner lining of the cornea is extremely delicate and any trauma which occurs may cause it to perish, resulting in a clouded cornea which will eventually need replacement. The limbal opening should never by any larger than needed to remove the cataract and to allow entrance of the intraocular lens optic. With newer instrumentation, a large cataract can be removed through an opening as small as 3½ mm. This ability for the lens optic, including the haptics, to enter a small opening is an important feature of the present invention.

The limbal opening, which is as small as possible, is the site where the trabecular meshwork is located. This structure is where internal eye fluid is drained after the internal eye structures have metabolized and depleted the fluid. If this structure is damaged excessively, it causes pressure in the eye to rise, resulting in glaucoma, pain and blindness. It is essential that the insertion of the lens and the fixation of the lens haptics damage as little of this internal structure as possible. Postoperatively, the smaller the incision, the less the astigmatism and visual distortion, and the less the risk of wound leakage and infection.

The internal dimension spanning across the anterior chamber from trabecular meshwork angle to the opposite side is different from person to person. This dimension can range from approximately 10 mm to approximately 14.5 mm, and is dimensionally different vertically and horizontally. The size of the anterior chamber lens to be inserted has previously been calculated by imperfect means. Although the calculation may be accurate for a vertical meridian, if the lens is inserted horizontally it will be of incorrect size. The lens of the present invention will fit any size of eye, in any operative situation, even an eye that is oval, rather than round in shape.

According to the invention, the lens, having connecting means to enable fixation into the eye, may be inserted through a small incision not any larger than the smallest diameter of the lens portion of the device. The lens itself is generally circular, though it may be oval or of rounded rectangular or other appropriate shape.

Figure 1:
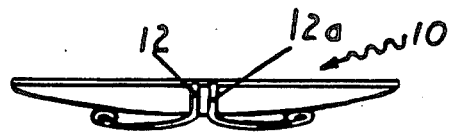
FIG. 1 is an end view of one embodiment of the invention, having two pairs of opposing haptics.
Figures 3, 4:
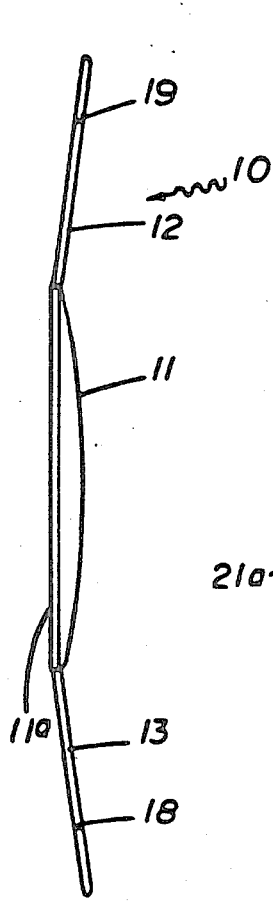
FIG. 3 is a side view of FIG. 1.
FIG. 4 is a side view of FIG. 2.
Figure 5:
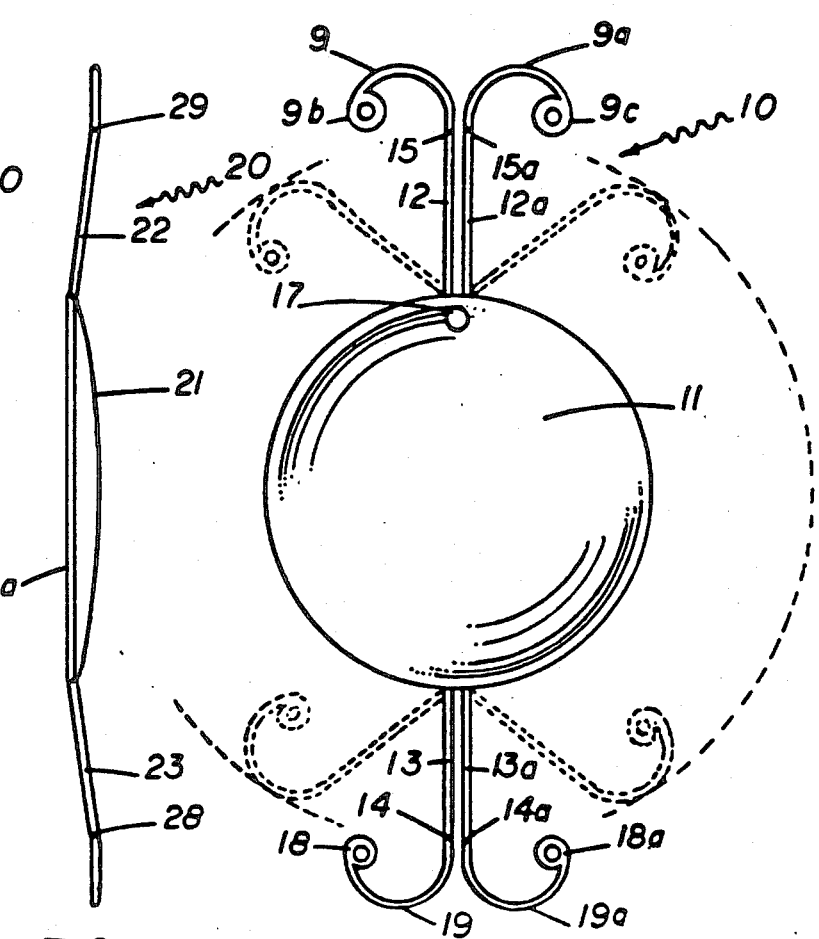
FIG. 5 is a top view of FIG. 1 in which the broken lines show the haptics compressed within the eye.

Referring now to embodiment 10 illustrated in FIGS. 1, 3 and 5, there is illustrated an optic 11 having an end positioning hole 17, useful for manipulating the optic into the correct position. Adjacent the positioning hole 17 is a pair of closely spaced, outwardly extending, flexible, straight, connecting haptic portions 12 and 12a extending to form curved open end portions 9 and 9a which are offset from the straight portions by crimps 15 and 15a. The crimps enable extra flexibility of the haptic portions. The end portions curve away from one another and may optionally terminate in closed circular portions 9b and 9c, or may have curved open end portions.

On the opposite side of optic 11 and diametrically opposed to haptics 12 and 12a are similar flexible haptics 13 and 13a extending outwardly and curving away from one another at crimps 14 and 14a to form curved open end portions 19 and 19a optionally terminating in closed circular loops 18 and 18a. The straight, connecting, haptic portions join the optic on the edge of its flat back portion 11a. The illustrated vault is about 7.5 degrees.

Figure 2:
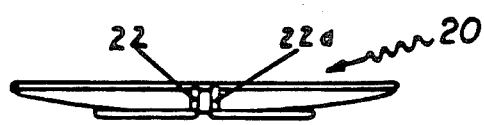
FIG. 2 is an end view of another embodiment having two pairs of opposing haptics, differently vaulted.

The embodiment 20 illustrated in FIGS. 2 and 4 is similar to the embodiment illustrated in FIGS. 1, 3 and 5. One pair of closely spaced flexible haptics 22 extends outward from the end of optic 21. Diametrically opposed is a second pair of closely spaced similar flexible haptics 23 which extend out from the other end of optic 21. The curved open end portions of the haptics are offset by crimps 28 and 29 in a different plane from that of FIG. 3 but are similarly joined to the edge of the flat back portion 21a of the optic. The curved end portions optionally terminate in closed loops. The illustrated vault is about 7.5 degrees from the optic edge to the crimp where it becomes parallel to the flat back portion of the optic.

The embodiment 40 illustrated in FIGS. 7, 9 and 10 is of a slightly different configuration from that of the previous two embodiments. Three flexible haptics, 42, 43 and 44 extend from the optic portion 41 attached to the edge of the optic at spaced intermediate positions. Each of the haptics has an open curved end portion, optionally terminating in a closed loop offset from the straight connecting portion of the haptic. Flexible haptic 42 is offset at crimp 42b and curves clockwise. Spaced across from haptic 42 is haptic 44 having curved end portion 44a, offset at crimp 44b, facing counter clockwise, i.e. facing the curved end portion of haptic 42. Haptics 42 and 44 are spaced apart a considerable distance of the optic and positioning hole 47 is also quite clear of the ends of the haptics. Haptic 43 is attached in a direction opposite to haptic 42 and has crimp 43a, counterclockwise curved open end portion 49 and optional terminal closed end circular loop 48. The illustrated vault is about 7.5 degrees from the optic edge to the crimp where it becomes parallel to the flat back portion.

Embodiment 30, illustrated in FIGS. 6 and 8, is similar to that of FIGS. 7, 9 and 10, except that the haptics are offset at a slightly different angle. Thus, optic 31 which has a flat back portion 31a, has intermediate attachments to haptics 32, 33 and 34 with the curved end portions being offset at crimps 32a, 33a and 34a. The illustrated vault is about 7.5 degrees.

Figure 12:
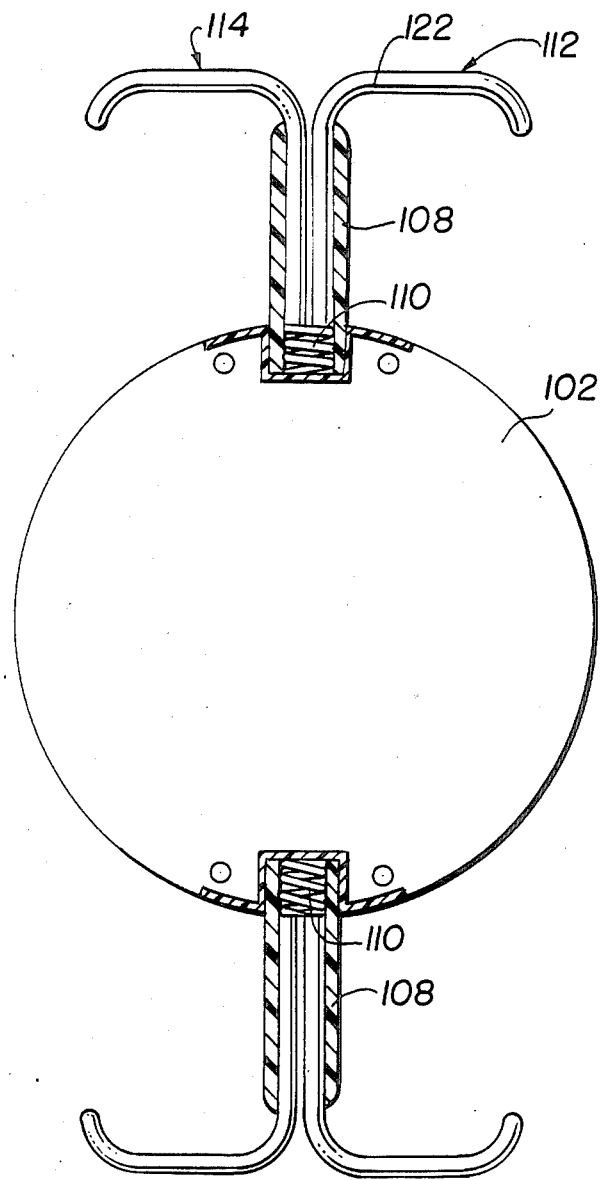
FIG. 12 is a top view of the optic of FIG. 11 in the maximally compressed position.
Figure 13:
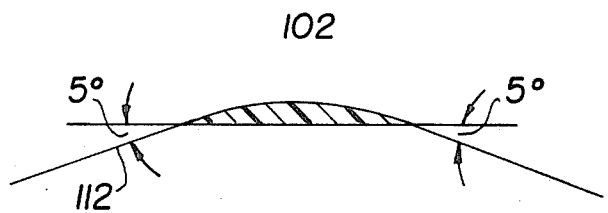
FIG. 13 is a schematic view of the optic of FIG. 11 showing the angle of vaulting.
Figure 14:
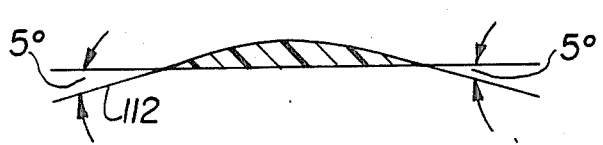
FIG. 14 is a schematic view of the optic of FIG. 12 showing the angle of vaulting.
Figure 16:
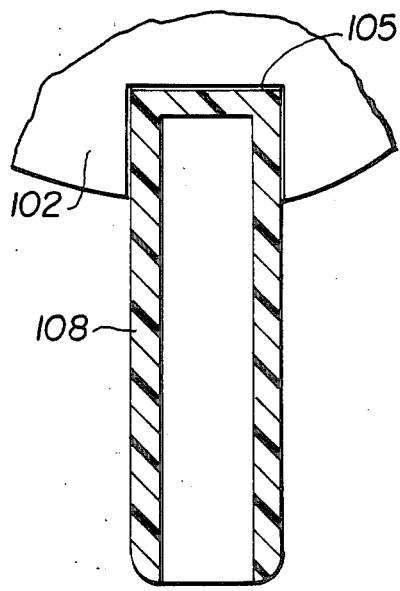
FIG. 16 is a detail of a lens optic in which the housing is omitted.
Figure 17:
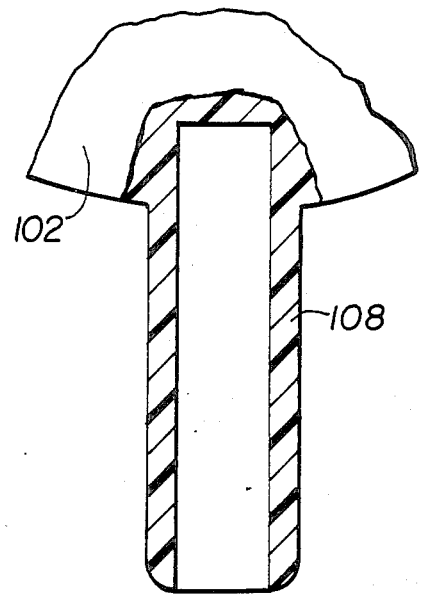
FIG. 17 is a detail of a lens optic in which the cylinder and housing are molded integrally with the lens optic.

Referring to FIGS. 11 to 19, in which like numerals represent like parts, lens optic 102, which may, for example, be a circular optic of 5 mm in diameter, and be molded from plastic, such as polymethylmethacrylate or silicone, has four positioning holes 104, each measuring approximately ¼ mm in diameter, located one on each side of each notch 105 into which optional housing unit 106 may be inserted. Notch 105 is vaulted at any desired angle, optionally 5° to 7.5°, and preferably 5°. FIG. 11, shows two diametrically opposed housing units 106, each one having a positioning hole 104 located adjacent each side of it. A cylinder 108 is inserted into the lens optic 102 at the desired angle of vaulting, as shown in FIGS. 13 and 14, or cylinder 108 may be integrally molded into the lens at the desired angle of vaulting as shown in FIG. 17. The angle of vaulting is preferably 5°, since the haptics are very flexible, or the angle of vaulting may have another value according to the size and shape of the eye in which the device is inserted. Spring 110, which may be a coil, is located within cylinder 108, and has one end attached to, or resting on, the base of, cylinder 108. Haptics 112, 114 are attached to the upper end 116 of the spring 110, preferably by gluing, soldering, threading, or the spring may be a molded extension of haptics 112, 114. The lower end 118 of spring 110 rests in, or is secured to, base 120 of cylinder 108. Cylinder 108 may have a base 120 to which lower end 118 of spring 110 is attached, or cylinder 108 may be open ended, in which case lower end 118 of spring 110 rests on, or is secured to optional housing unit 106. In one embodiment of the invention, shown in FIG. 16, housing unit 106 is omitted and lens optic 102 is shaped with notched portions 105 for receiving cylinder 108.

Figure 18:
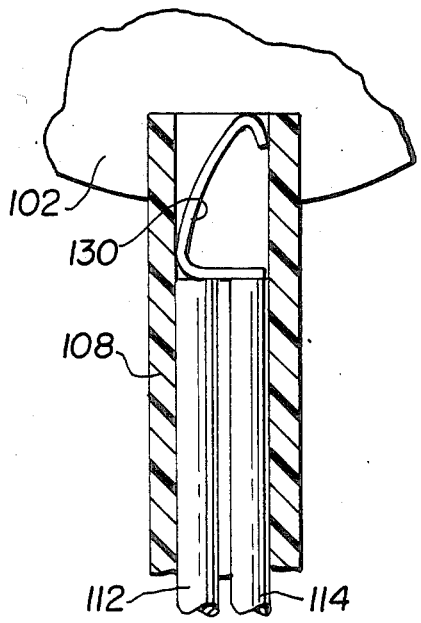
FIG. 18 is a detail of a lens optic showing use of a C-spring.
Figure 19:
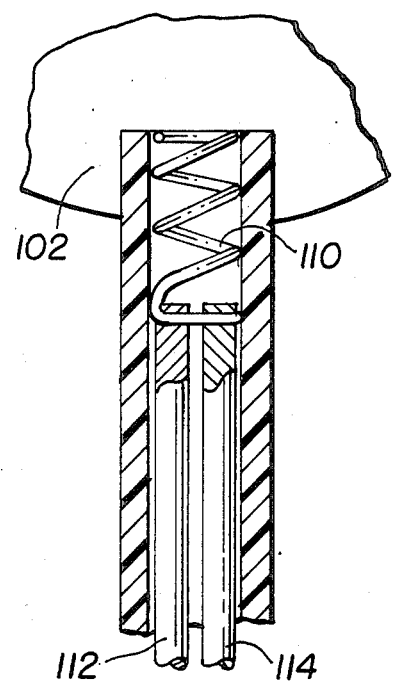
FIG. 19 is a detail of a lens optic showing a coil spring threaded through the ends of the haptics.

The spring and the haptics may be made of metal, such as stainless steel or plastic, such as polymethylmethacrylate, polypropylene, or silicone, and are very readily compressible. When non-compressed, spring 110 is approximately 1½ mm in length. When maximally compressed, spring 110 is ½ mm in length. The spring may be a coiled spring 110 as shown in FIGS. 11 to 13, or a C-spring 130 as shown in FIG. 18. Cylinder 108 measures approximately 2½ mm in length, and is just wide enough to contain two mirror-image flexible haptics 112, 114, side-by-side. Closely-spaced, paired flexible haptics 112, 114 extend outwardly from cylinder 108 and each has a straight portion 122 attached at one end to upper end 116 of spring 110 and a curved end portion 124, attached to straight portion 122. End portions 124 curve outwardly away from one another, each end 124 terminating in a smooth rounded portion 126, or, optionally, having a closed end (as shown in FIG. 5). The haptic may alternatively rest on the upper end 116 of spring 110, or spring 110 may be threaded through the lower ends of the haptics, as shown in FIG. 19. The flexible haptics may be made of wire or of solid plastic material, as described, and are suitably ⅓ mm diameter.

FIG. 11 shows the lens ready for insertion into an eye, and as it would appear inserted in a large eye of approximately 14½ mm diameter. FIG. 12 shows a device in the maximally compressed position, as it would appear in a small eye of approximately 10 mm diameter. For use in an eye of diameter between 10 mm and 14½ mm the spring is compressed an intermediate amount and the haptic are curved an intermediate amount, equilibrium being reached between curvature of the haptics and compression of the coiled spring. The haptics are extremely flexible, and the lens fits comfortably in any size of eye.

Lens 102 has notches 105 for insertion of each optional housing unit 106, and for insertion of cylinder 108. Notch 105 is angled to the flat back of the lens according to the angle of vaulting required. In a short eye (10 mm diameter), there is little vaulting due to the short extension of the haptics from the lens, as shown in FIG. 14. In a longer eye (14 mm diameter), there is greater vaulting due to the longer extension of the haptics from the lens, as shown in FIG. 15, The angle of vaulting is constant at approximately 5° flexion for a housing unit of ½ mm in depth.

FIG. 15 shows an alternative embodiment in which lens optic 128 is of rounded rectangular shape. Another alternative is for the lens optic to be oval in shape. Rounded rectangular lens 128 is approximately 5 mm in length and 3½ mm in width. A housing unit 106 and/or cylinder 108 is received in each narrow end (approximately 3½ mm) of the lens. This rounded rectangular form is particularly suitable for a phakoemulsification incision, which may be as small as 3½ mm, allowing implantation of the lens even using ultra microscopic intraocular surgery or in secondary implantation. The 5° vault of the housing unit 106 is the same for a rounded rectangular or oval lens optic as for a circular lens. The other components of the device are also similar to those used for a circular lens optic.

The flexibility of the lens is demonstrated by FIGS. 12 and 14 showing the lens in maximally compressed position as when inserted in a 10 mm diameter eye. Spring 110 and paired haptics 112, 114 descent within cylinder 108 close to the base of housing unit 106. Flexible haptics 112, 114 are shown flexed outwardly away from each other, away from the paired parallel vertical orientation to a mirror image horizontal orientation, thereby effectively shortening the longitudinal dimension of the lens and allowing implantation into a small eye, while retaining the haptics in the elongated position during insertion of the device into the eye through a very small incision. The extreme flexibility which is enabled by the cylinder-spring design of the lens of the invention allows the lens to fit in the anterior chamber of any size of human eye, allowing stability, security and comfort.

Whether the patient has had complicated or simple cataract surgery, which may be intracapsular, extracapsular or phakoemulsification cataract surgery, the optic, which rests slightly anterior to the pupil, should be of appropriate power for the eye, as calculated preoperatively. Placement of the optic in the anterior chamber also prevents pupil block glaucoma. If it becomes apparent that laser treatment will be needed to open a clouded posterior capsule, the lens will not be damaged during the laser treatment, since the lens is never in apposition to the posterior capsule. The lens can thus be used for primary, secondary or complicated implantation surgery. The lens of the invention features each of the following attributes: good lens stability and fixation in the anterior chamber (which requires at least three fixation points to prevent floating, rocking and rotation against the cornea and dislocation in the anterior chamber); lens haptic flexibility to prevent glaucoma, dislocation, cornea damage, inflammation, and tissue tenderness and pain; one size to fit all eyes; compressibility from 14.5 mm to 10 mm; situation of the device in the anterior chamber without damage to the internal structures; and insertion through a small incision no larger than the smallest diameter of the lens.

An anterior chamber lens of the invention that can flex over a span of 4.5 mm can be considered for implantation into the eye of an infant or child. As the child and the eye grow, the haptics will expand and maintain the central position of the lens. This anticipates, and provides a solution for, the problem of selecting the proper size of lens, knowing that eye measurements change with time as the child matures.

Good anterior chamber fixation is necessary, and requires at least three fixation points. The lens of the invention preferably provides four fixation points (four haptics). An anterior chamber lens must be equally flexible in all directions to obtain centration, and this is provided by the cylinder-spring design of the invention which enables the distal 2.75 mm end of the haptic to compress upon itself and flex at its union with the proximal 1 mm straight portion of the haptic which also has the ability to compress at its junction with the optic, by means of the cylinder-spring compression feature.

The lens of the invention is also equally suitable for as a posterior chamber lens.

While the invention has been described above with respect to certain embodiments thereof, it will be appreciated that various changes and modifications may be made without departing from the spirit and scope of the invention.

What is claimed is:

1. An intraocular lens adapted for insertion into and fixation in the anterior chamber of substantially any size of human eye, said lens comprising a lens optic portion and fixation means for fixing the lens optic portion in any size of eye, said fixation means comprising haptic means for accommodating the lens optic portion in the eye and spring means for facilitating fixation, said spring means extending outwardly from the lens optic portion, said intraocular lens being insertable in the eye through an incision of substantially the same diameter as the smallest diameter of the lens optic portion, wherein the haptic means comprises a pair of haptics each having a straight portion in contact with the spring means, said straight portions extending outwardly from the lens in closely spaced parallel position, and a curved end portion for fixing the haptic means in the eye connected to each straight portion, the curved end portions facing away from each other, and wherein the spring means are increasingly compressed as the haptic means are increasingly flexed.

2. An intraocular lens of claim 1 wherein the lens optic portion comprises two diametrically opposed means for receiving the fixation means.

3. An intraocular lens of claim 2 wherein the means for receiving the fixation means comprise housing means.

4. An intraocular lens of claim 1 wherein the fixation means comprises cylinder means for receiving the spring means.

5. An intraocular lens of claim 3 wherein the housing means are formed integrally with the lens optic portion.

6. An intraocular lens of claim 5 wherein the housing means further includes cylinder means formed integrally with the lens optic portion.

7. An intraocular lens of claim 4 wherein the spring means comprises a material selected from the group consisting of stainless steel, polymethylmethacrylate and silicone.

8. An intraocular lens of claim 1 wherein the haptic means comprises a member selected from the group consisting of stainless steel, polymethylmethacrylate, and polypropylene and silicone.

9. An intraocular lens of claim 1 wherein the lens optic portion comprises a material selected from the group consisting of polymethylmethacrylate and silicone.

10. An intraocular lens of claim 1 wherein the lens optic portion comprises vaulted housing means.

11. An intraocular lens of claim 10 wherein the vaulting is at a 5° angle to the back of the lens optic portion.

12. An intraocular lens of claim 10 wherein the vaulted housing means are formed integrally with the lens optic portion.

13. An intraocular lens of claim 1 comprising a lens optic portion of rounded rectangular shape.

14. An intraocular lens of claim 1 comprising a lens optic portion of oval shape.

15. An intraocular lens adapted for insertion into and fixation in the anterior chamber of substantially any size human eye, comprising an optic portion having a flat back portion and three flexible haptics attached to the edge of said flat back portion, each said haptic being of substantially identical size and shape and comprising a straight, connecting portion attached to the edge of the flat back portion at a slight angle to provide a desired vault, said connecting portion terminating in a crimp portion from which an open curved end portion extends outwardly, each haptic being attached in spaced apart intermediate positions on the edge of said back portion; a first haptic facing clockwise, a second haptic facing counterclockwise and a third haptic being attached close to the point of attachment of one of the other two haptics, but facing the opposite direction, the lens being insertable into the eye through an incision of the same size as the smallest diameter of the lens.

* * * * *